United States Patent [19]

Lee et al.

[11] Patent Number: 4,908,208

[45] Date of Patent: Mar. 13, 1990

[54] MATRIX FOR RELEASE OF ACTIVE INGREDIENTS

[75] Inventors: Chi-Long Lee; Gerald A. Gornowicz, both of Midland, Mich.

[73] Assignee: Dow Corning Corporation, Midland, Mich.

[21] Appl. No.: 184,731

[22] Filed: Apr. 22, 1988

[51] Int. Cl.[4] .............................................. A01N 25/08
[52] U.S. Cl. ...................................... 424/409; 424/78; 424/76.3; 424/84; 424/486; 71/3; 523/102; 528/28
[58] Field of Search .......................... 528/28; 525/474; 424/78, 84, 486, 409; 523/102; 512/4; 71/3

[56] References Cited

U.S. PATENT DOCUMENTS

| | | | |
|---|---|---|---|
| 4,136,250 | 1/1979 | Mueller | 528/29 |
| 4,235,988 | 11/1980 | Fildes et al. | 528/79 |
| 4,554,155 | 11/1985 | Allan et al. | 424/22 |
| 4,631,329 | 12/1986 | Gornowicz et al. | 528/28 |
| 4,703,070 | 10/1987 | Locko | 523/102 |
| 4,793,555 | 12/1988 | Lee et al. | 239/6 |

FOREIGN PATENT DOCUMENTS 0126791 12/1984 European Pat. Off. ............... 512/4

OTHER PUBLICATIONS

Yilgör, I. "Segmented organosiloxane copolymers. 1. Synthesis of siloxane-urea copolymers", Polymer, vol. 25 pp. 1800–1806.

Tyagi, D. "Segmented organosiloxane copolymers. 2. Thermal and mechanical properties of siloxane-urea copolymers", Polymer, vol. 25 pp. 1807–1816.

*Primary Examiner*—Lewis T. Jacobs
*Assistant Examiner*—Ralph H. Dean, Jr.
*Attorney, Agent, or Firm*—Allan O. Maki

[57] ABSTRACT

A matrix for delivery of active substances such as fragrances and pheromones into the atmosphere is provided which matrix is active substance permeable (including to hydrophilic substances) and is formed of a copolymer which can be softened sufficiently at temperature between 45° C. and 160° C. to incorporate the substances therein without damage caused by heat or chemical reactions, the matrix being formed of a substantially linear block copolymer which is a reaction product of a polydiorganosiloxane which forms soft segments in said reaction product and a diisocyanate which forms hard segments, said copolymer having a glass transition temperature between 45° C. and 160° C. said soft segments comprising from 70 to 99 percent by weight, based on the weight of said copolymer, the average molecular weight of the copolymer being between 15,000 and 500,000.

7 Claims, No Drawings

MATRIX FOR RELEASE OF ACTIVE INGREDIENTS

BACKGROUND OF THE INVENTION

1. Field of the Invention

This invention relates to the controlled release into the atmosphere of active substances such as air fresheners, fragrances or pheromones from a solid carrier or matrix. More particularly, this invention relates to matrices which are solids at room and ambient temperatures which are useful for controlled release of such active substances. The matrices have a glass transition temperature such that various active substances can be incorporated by melting or softening the matrix composition and mixing the active substance into the softened composition.

2. Description of the Prior Art

Matrices have hithertofore been used as reservoirs for containing and releasing active substances such as fragrances or pheromones. Representative of this prior art is U.S. Pat. No. 4,703,070 to Locko, et al, issued Oct. 27, 1987. Hithertofore, as described, for example, in that patent, the active substances were incorporated into resinous or elastomeric materials which were subsequently cured or cross-linked. It has not been feasible to incorporate many types of active substances into such systems in which the cure is not complete at the time the substance is incorporated into the composition, because the active substance may be deleteriously affected by either the vulcanizing temperatures which in many cases are required to cure the polymer, by the ingredients of the prepolymer, which may contain reactive components that react with the active substance, or the curing agent which may interact with some active substances. In the case of the latter interactions the active substance inhibits the curing agent in some cases, while the curing agent affects the characteristics of the active substance in other cases.

An objective of this invention is to provide materials for matrices that enable the migration therethrough of a variety of active substances and which can be melted or softened to the extent that such substances can be admixed therein at relatively low temperatures, ie., about 45° C. to 160° C., which temperature in each case is low enough to avoid thermal damage to the active substance. The matrices of the present invention are thermoplastic materials which do not require the presence of curing agents, prepolymers, or catalysts. By elimination of the need of using such ingredients which might themselves impair the efficacy, odor or other characteristics of the active substance which is to be released, a number of problems encountered with the prior art thus are eliminated.

SUMMARY OF THE INVENTION

The present inventors discovered that certain members of the broad class of segmented block copolymers are unique by virtue of (1) their high permeability to the ingredients of various mixtures of active substances including those of a hydrophilic type, (2) their resistance to dissolving and/or degradation by the active ingredients and (3) their ability to be fabricated into composite devices by melting at relatively low temperatures (45° C. to 160° C.) for incorporation therein of active substances. The present copolymers comprise a hard segment which comprises an organic diisocyanate or optionally is derived from the reaction of an organic diisocyanate with a diol or diamine and a soft segment (or oligomer) containing one or more polydiorganosiloxane units. Matrices formed from these copolymers are particularly useful for containing and controlling the rate of release of a broad spectrum of active substances. Representative active substances which can be incorporated into the matrices of this invention include insect sex pheromones, insect repellents, fragrances, air fresheners, and air deodorizers. The matrix materials of the present invention can be characterized as low strength rubbers or high strength gels.

Briefly summarized, the present invention provides, matrices for containing an active ingredient; said matrix comprising a substantially linear thermoplastic block copolymer which is a reaction product of a polydiorganosiloxane having end groups, preferably amino functional groups, which are reactive with an isocyanate to form polyurethane or polyurethane-urea linkages, which polydiorganosiloxane units form "soft" segments in said reaction product; and a diisocyanate which forms "hard" segments. Said copolymer has a glass transition temperature between about 45° C. and 160° C. and said soft segments comprise from about 70 to 99 percent by weight, based on the weight of said copolymer, the average molecular weight of said soft segments being between 1200 and 30,000. Chain extenders such as low molecular weight alkylene diols or diamines can optionally be included in the polymer. Also optionally, polyalkylene oxides can be incorporated into the polymer to increase its hydrophilicity, thereby improving the permeability of the polymer as to hydrophilic or ionic active agents.

DETAILED DESCRIPTION OF THE INVENTION

This invention provides a matrix material for delivery devices for active substances in which the matrix comprises a layer of a solid thermoplastic, linear, segmented copolymer having a glass transition temperature between about 45° C. and 160° C. where said layer is inert with respect to and permeable with respect to said active substance. The layer is a cohesive solid at ambient temperatures and is preferably about 0.01 to 1 cm. thick and is formed of a substantially linear segmented (block) copolymer comprising from about 1 to 30 weight percent of "hard" segments consisting essentially of polyurethane or polyurea units derived from an organic diisocyanate and, if desired, an alkylene diol or similar difunctional chain extender, and from 70 to 99 weight percent of "soft" segments comprising from 15 to 99 percent by weight, based on the weight of said copolymer, of a hydrophobic portion consisting essentially of one or more polydiorganosiloxane units. In the case of a hydrophilic active agent, from 0 to 65 percent by weight, based on the weight of said copolymer, of a hydrophilic portion consisting essentially of at least one polyalkylene oxide unit, preferably polyethylene oxide (PEO), can be included in the polymer chains.

This invention also provides an improved method for forming a matrix for an active substance delivery device, which comprises admixing an active substance into a molten or softened copolymeric material at temperatures which do not cause thermal damage to the active substance, and then cooling the resultant composition to form the composite matrix. The composition can be formed into matrices of the desired size either by casting directly from the softened state or cutting from a sheet of the composition formed by cooling the mixture.

The molecules of block copolymer that constitute the matrices of the present invention contain at least one segment of a "hard" polymer and at least one segment of a "soft" polymer. It is understood in the art that the terms "hard" and "soft" as applied to segments of block copolymers refer to the relative glass transition temperatures ($T_g$) of the segments. The hard segment has a substantially higher glass transition temperature than the soft segment.

The hard segment of the present copolymers is a polyurea or polyurethane derived from an organic diisocyanate and, optionally, a low molecular weight diol or diamine, sometimes referred to as a chain extender. Any of the available aliphatic, aromatic or cycloaliphatic diisocyanates can be used to prepare the polyurea or polyurethane portion of these copolymers. Preferred diisocyanates include but are not limited to p-tolylene diisocyanate (TDI), 4,4'-diphenyl methane diisocyanate (MDI) and 4,4'-dicyclohexylmethyldiisocyanate ($H_{12}MDI$), and isophorone diisocyanate (IPDI).

The chain extender portion of the polyurethane can be any of the available aliphatic diols or diamines containing from 2 up to about 10 carbon atoms. Diols containing from 2 to 4 carbon atoms are preferred, based on the availability and environmental compatibility of these compounds.

The hard segment constitutes from about 1 to 30 weight percent of the copolymer, preferably from 3 to 25 weight percent, and the molar ratio of hard segment (diisocyanate and aliphatic diol units) to soft segments (polydiorganosiloxane and polyalkylene oxide units) is from 1:1 to 5:1. The soft segment of the present copolymers may include a hydrophilic and a hydrophobic portion. The hydrophobic portion of the copolymer molecules consists essentially of at least one sequence of from 15 to about 400 diorganosiloxane units, and these sequences constitute from 15 to 99 weight percent, preferably from 40 to 97 weight percent, of the copolymer. The preferred polydiorganosiloxane is polydimethylsiloxane (PDMS), because of its high permeability, and commercial availability. Methods for preparing functionally substituted polydiorganosiloxanes and copolymerizing these polymers with diisocyanates and other organic monomers are known in the art and do not form part of this invention. See for example, Gornowicz et al U.S. Pat. No. 4,631,629. The preferred method is, however, the reaction in a suitable solvent of a diamino terminated polydiorganosiloxane oligomer with an approximately stoichiometric amount of an organic diisocyanate. The mixture is then reacted with a quantity of a low molecular weight alcohol, such as ethanol to make certain that there are no unreacted isocyanate groups remaining in the mixture.

The hydrophilic portion of the soft segment consists essentially of at least one sequence per copolymer molecule of from 5 to 75 ethylene oxide units, which can be present as part of the linear portion of the copolymer. The alkylene oxide units, which are preferably ethylene oxide units constitute from 0 to 65 weight percent of the copolymer.

The optimum molecular weight range for a given copolymer will be determined by the desired physical properties of the copolymer, such as melt viscosity, tackiness, and particularly the glass transition temperature of the hard segment of the copolymer. The weight average molecular weight is preferably from 15,000 to about 500,000, preferably 25,000 to 300,000. If a matrix is prepared from a thermoplastic copolymer of this invention, the weight average molecular weight of the copolymer is typically in the range of from 25,000 to about 300,000 to provide copolymers which melt (or soften to a degree sufficient to permit admixture into the polymer of active substances) at temperatures which are in the range of about 45° C. to 160° C. The preferred softening temperature in each case is dependant on the heat sensitivity of the particular substance incorporated into the matrix.

The specific substances used are not critical to this invention The term "active substance" is to be construed in its broadest sense as a material which is intended to produce some beneficial fragrance, odor, or effect after its release into the atmosphere. Representative examples of active substances include synthetic perfumes, fragrances such as natural essential oils, insect repellants, air deodorizers, bactericides, herbicides, plant growth regulators, and sex pheromones of insect pests. Examples of these substances include lemon oil, clove leaf oil, cedar wood oil, ylang oil, rose absolute, jasmin absolute, alcohols such as citronelli or cedrol, or acetates, esters, or aldehydes of such alcohols. Examples of the latter include citronellal, vanillin, citral and cinnamaldehyde. Other substances which produce desired scents will be apparent to those skilled in the art.

As used herein, a substance is considered to be oleophobic if the solubility of the substance in mineral oil is less than about 100 mg/g. A substance is considered to be "highly polar" when the percent ionization of the substance in an aqueous medium is at least about 95%. This occurs when the pKa of the active substance differs from the pH of the reservoir by an absolute value of at least 1.3. The pKa of a active substance is the pH of an aqueous solution in which 50% is in the unionized base or acid form.

Methods for preparing diorganosiloxane/polyurethane urea-oxyethylene copolymers are described in patents and other literature, see for example, Tyagi et al, "Segmented organosiloxane copolymers", *Polymer*, Vol. 25, pp 1807–1816. In accordance with a preferred method a liquid amino functional polydiorganosiloxane containing from 15 to about 400 repeating units per molecule and a monofunctional isocyanate-reactive group such as

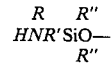

at the two terminal positions is reacted with the organic diisocyanate by heating the mixture in the presence of a suitable catalyst. Other isocyanate reactive groups which can be substituted include HOR'Si— and HSR'Si—. In the foregoing the aliphatic diol that optionally forms part of the hard segment is then added to the reaction mixture and heating continued until all of the isocyanate is reacted, which typically takes an additional 2 to 16 hours. The reaction is preferably conducted under an inert atmosphere such as nitrogen using as the reaction medium one or more organic liquids such as toluene, tetrahydrofuran (THF), or dimethylformamide (DMF) or mixtures of such solvents that will dissolve all of the reactants and the resultant copolymer.

The substituents represented by R and R″ in the preceding formula are monovalent hydrocarbon radicals and R′ represents an alkylene radical. Each of the R, R′, and R″ radicals may be the same or different.

The present block copolymers are thermoplastic and can be processed to form layers using any of the known techniques for fabricating thermoplastic organic polymers. These techniques include but are not limited to casting, pressing, calendaring, and extrusion of bulk copolymers and dissolving the copolymers to form solutions that are then applied to a suitable substrate to form coatings or layers. The active substance-containing copolymer can also be formed into discrete spheres of about 0.5 to 5 mm in diameter by dispersing the molten copolymer into cold water.

The following examples describe preferred embodiments of the present invention. The examples should not be interpreted as restricting the scope of the invention as defined in the accompanying claims. Unless otherwise specified, all parts and percentages in the examples are by weight.

EXAMPLES

Copolymer Synthesis

Urethane-urea copolymers were prepared using procedures outlined in U.S. Pat. No. 4,631,629. The mole ratio of diisocyanate to low molecular weight alkylenediol, chain extender to aminoalkyl endblocked PDMS plus polyalkylene oxide was kept at 3/2/1. Urea copolymers were prepared following a procedure similar to that of Yilgor; et.al.[1]

[1]Yilgor, I.; Sha'ban, A. K.; Steckle, W. P.; Tyagi, D.; Wilkes, G. L. and McGrath, J. E., Polymer, 1984, Vol 25, 1800–1806.

EXAMPLE 1

$H_{12}$MDI (53.0 g, 0.398 eq) and toluene (1450 g) was added to a 3 liter, 3 neck flash equipped with and air stirrer, heating mantel, reflux condenser, addition funnel and nitrogen atmosphere. N-methylamino-iso-butyl endblocked PDMS (1397.2 g, 0.398 eq) was added dropwise. After all the siloxane had been added, the reaction was stirred for 1 hour at room temperature and then poured into glass baking dishes. Most of the toluene was allowed to evaporate in a hood. Residual toluene was then removed in a vacuum oven to give pure Copolymer III in Table I. A slight excess of isocyanate can be used to make sure all the amine endblocked PDMS is reacted. This gives copolymers with isocyanate ends which are quenched with excess ethanol before removing the solvent. Copolymer I was prepared in the same manner.

EXAMPLE 2

$H_{12}$MDI (53.0 g, 0.397 eq) and toluene (285 g) was put in 3 liter, 3 neck flask equipped with an air stirrer, temperature controller, dry nitrogen atmosphere and addition funnel. A solution of N-methylamino-iso-butyl endblocked PDMS (485.8 g, 0.132 eq) in toluene (500 g) and 0.3 ml of 10% dibutyltin dilaurate (DBTDL) in toluene was added slowly. Temperature was increased to 100° C. for one hour. 1,4-Butanediol (BD) (11.9 g, 0.265 eq) was added. After 20 minutes the reaction started to become hazy. Tetrahydrofuran (THF) (100 ml) was added and the reaction cleared. After 5 minutes the reaction began to turn hazy again, THF (100 ml) was added to make it clear. After 15 minutes the haze began to form and another 100 ml of THF was added. This procedure was repeated 3 more times with 200 ml aliquots of THF. A total of 900 ml of THF was added. The reaction stayed clear and was heated at reflux overnight. The solvent was removed to give Copolymer IV. Copolymer II was prepared in the same manner.

EXAMPLE 3

Using a similar procedure as above, $H_{12}$MDI (43.3 g, 0.325 eq, 12.3%) was reacted with a 50 dp N-methylamino-iso-butyl endblocked PDMS (213.5, 0.13 eq, 60.7%) and PEO 1540 (91.7 g, 0.12 eq, 26.1%) using DBTDL (0.3 ml of 10% solution in toluene). Reaction was heated 1 hour at 100° C. Then 1,4-butanediol (3.4 g, 0.075 eq, 1.0%) was added. Reaction was heated overnight. Solution was poured into baking dishes and most of the solvent was allowed to evaporate in a hood. Residual solvent was removed in a vacuum oven to give Copolymer V.

EXAMPLE 4

Copolymer I (3 g) was heated in a beaker in an oven at 110° C. Trimedlure (a synthetic insect attractant for the Mediteranean fruit fly manufactured by Agron, Inc.) (3 g) was added and mixed with a spatula. Upon cooling this mixture formed a viscous liquid. An aliquot of this mixture was mixed with more Copolymer I to reduce the Trimedlure loading to 10% (w/w). Part of this hot solution was transferred to a shallow metal cap, 1 cm diameter. Upon cooling a soft rubber containing Trimedlure was obtained. This was placed in a room kept about 20° C. and 50% relative humidity (RH). The release of the Trimedlure was followed by weighing the cap periodically. The release rate (dQ/dt) is reported in Table II. In a similar manner a matrix of Copolymer I containing 20% Trimedlure was prepared and the release rate determined.

EXAMPLE 5

Copolymer II (0.6 g) and Trimedlure (1.4 g) were heated at 110° C. for a few hours. Periodically the copolymer was stirred with a spatula and gradually a homogeneous solution was formed. Part of the solution was poured into a shallow metal cap. Upon cooling a rubbery matrix containing 70 weight % Trimedlure was obtained. The matrix was dry to the touch. A sample of this matrix was heated about 100° C. overnight in a vacuum oven to make sure that the loading of Trimedlure remained about 70% while the copolymer was dissolved and the matrix was formed. The residue, Copolymer II, was 28.1% of the original sample. Therefore the matrix contained 71.9% Trimedlure. The release rate is reported in Table II.

The loading of Trimedlure was increased to 80 and 90% by adding more Trimedlure to aliquots of the 70% Trimedlure sample above at 110° C. Upon cooling the resulting solutions, soft rubbery matrices were obtained. These were dry to the touch. However, after 3 days small droplets of liquid formed on the surface of the matrix containing 90% Trimedlure. The release rate for the matrix with 90% Trimedlure is reported in Table II.

EXAMPLE 6

A matrix containing 70% Trimedlure in Copolymer IV was made in the same manner. The hot solution was poured into a metal cap then allowed to cool. A dry, non-tacky, soft rubber was obtained. The release rate of Trimedlure was measured as described above.

EXAMPLE 7

A solution (about 1 gram) of 80% Trimedlure and 20% Copolymer II was heated to about 100° C. then poured into rapidly stirred cold water. Spheres, approximately 2 mm diameter, formed. These were separated from the water and dried. The spheres do not stick together and could be easily used in an insect trap.

EXAMPLE 8

Copolymer 1 (3.0 g) was heated to about 100° C. and Gossyplure, (a insect pheromone for the pink boll worm manufactured by Agron, Inc.), (0.75 g) was mixed in with a spatula until a homogeneous mixture was obtained. This solution was cooled to a solid. About 1.5 grams of the solid was placed in a rectangular chase, 3.8×2.55 cm, and 0.1 cm thick, lined with Teflon release sheets and compression molded at 60° C. at 345 MPa for 30 seconds. The press was cooled with cold water to give a dry, rectangular slab with a surface area of 19.9 cm$^2$. The slab was hung in a room kept about 20° C. and 50% RH.

EXAMPLE 9

Copolymer III, a PDMS/polyethylene oxide/urea-urethane copolymer, (1.6 g) was heated at 100°–110° C. Trimedlure (0.4 g) was added and the mixture heated and stirred with a spatula until homogeneous, about 15 min. The solution was transferred to a metal cap (1.0 cm diameter) and kept warm until the cap was filled uniformly. Upon cooling to room temperature a soft, dry, non-tacky matrix was obtained. The release rate, dQ/dt, was measured as above and reported in Table II.

EXAMPLE 10

Copolymer III (2.0 g) was heated in a 2 oz vial at 100°–110° C. Dursban ® R, an insecticide manufactured by Dow Chemical Co., (2.0 g) was added and the mixture was stirred with a spatula until an uniform white paste was obtained. This was transferred to a rectangular chase, 3.8×2.55 cm, and 0.1 cm thick, lined with Teflon release sheets. A steel plate was laid on top of the sample and then it was pressed flat. Upon cooling a rectangular slab with 19.9 cm$^2$ total areas was obtained. This was suspended in 200 ml of 40/60 (v/v) polyethylene oxide, 400 molecular weight, (PEG 400) and water solution in a Ghannam-Chien membrane permeation apparatus.[2] Periodically a sample was removed and the absorbance at 288 nm was measure in a Bausch & Lomb Spectronic 2000 spectrophotometer. The concentration of Dursban ® R in solution was determined from a calibration curve. The release rate (dQ/dt) was calculated using the following formula:

$$dQ/dt = V(c/t^{0.5})/At^{*0.5}$$

Where V is the volume of liquid, $c/t^{0.5}$ is obtained from the initial linear slope of a plot of concentration versus the square root of time, A is the area of the sample and t* is the time required for the concentration to reach equilibrium. The release rate is reported in Table III.

[2] K. Tojo, Y. Sun, M. Ghannam, and Y. W. Chien. Characterization of a Membrane Permeation System for Controlled Drug Delivery Studies AICHE Journal, 31(5), 741–46 (1985).

EXAMPLE 11

Copolymer (2 g) was heated at 100°–110° C. A herbicide, 2,4-Dichlorophenoxyacetic acid (1.37 g), was added and the mixture was stirred with a spatula until a uniform dispersion was obtained. Then Et$_3$N (0.63 g) was added and uniformly mixed into the dispersion. Upon cooling a dry, rubbery mixture was obtained. A sample was compression molded at 60° C. at 138 MPa for 30 seconds and cooled to give a sample with a surface area of 19.9 cm$^2$. The release rate into distilled water was measured as described above and is reported in Table III.

EXAMPLE 12

Copolymer II (2.0 g) was heated at 100°–110° C. Benzyl alcohol (1.0 g), a component of fragrance formulations, was added and mixed in with a spatula. An aliquot was transferred to a 1 cm diameter metal cap and heated a few minutes at 100°–110° C. until it was filled the cap uniformly. Upon cooling an excellent matrix was obtained. Initially the surface was slightly tacky but it soon became dry. The release rate into the atmosphere was measured as described for Trimedlure examples and reported in Table II.

CONTROLS

Liquid Trimedlure and benzyl alcohol were put in metal caps, 1 cm diameter, and release rate was determined as above. The vapor pressure of Gossyplure is so low that no weight loss could be mearure from a 1 cm diameter cap. Therefore, the release rate for the Gossyplure was determined from an aluminum weighing dish, 5 cm diameter.

TABLE I

| | Composition and Properties of Thermoplastic Silicone Urethane Copolymers. | | | | | | |
|---|---|---|---|---|---|---|---|
| Copolymer | Weight % PDMS | Weight % BD | Weight % HMDI | Weight % PEO | Durometer (Shore A) | GPC* Mw | Tg deg. C |
| I | 89.2 | 0 | 10.8 | 0 | 57 | 100,000 | 59 |
| II | 77.7 | 4.1 | 18.2 | 0 | 74 | 138,000 | — |
| III | 96.5 | 0 | 3.5 | 0 | 30 | 150,000 | 65 |
| IV | 88.2 | 2.2 | 9.6 | 0 | 31 | 406,000 | 160 |
| V | 60.7 | 1 | 12.3 | 26.1 | 29 | 34,200 | 53 |

*Gel Permeation Chromatography (GPC).

TABLE II

| Controlled release of volatile active agents from thermoplastic silicone urethane copolymers into air. | | | | |
|---|---|---|---|---|
| Example | Co-polymer | Weight % Bioactive Agent | dQ/dt (mg/cm$^2$/day) | Matrix Integrity |
| Trimedlure | | | | |
| Control | none | 100 | 2.84 | |
| 4 | I | 10 | 1.94 | Excellent |
| 4 | I | 20 | 4.59 | Excellent |
| 5 | II | 70 | 3.93 | Excellent |
| 6 | IV | 70 | 2.89 | Excellent |
| 5 | II | 90 | 2.74 | Excellent* |
| 9 | III | 20 | 1.95 | Excellent |
| Gossyplure | | | | |
| Control | none | 100 | 0.006 | |
| 8 | I | 20 | 0.036 | Excellent |
| Benzyl Alcohol | | | | |
| Control | none | 100 | 14.1 | |

TABLE II-continued

Controlled release of volatile active agents from thermoplastic silicone urethane copolymers into air.

| Example | Co-polymer | Weight % B